United States Patent [19]

Neeb et al.

[11] 3,966,852
[45] June 29, 1976

[54] METHOD FOR PREPARING TEST SPECIMENS FOR ANALYSIS

[75] Inventors: Karl-Heinz Neeb; Werner Schweighofer; Hans-Jörg Weisse, all of Erlangen, Germany

[73] Assignee: Siemens Aktiengesellschaft, Munich, Germany

[22] Filed: Oct. 26, 1972

[21] Appl. No.: 300,963

[30] Foreign Application Priority Data
Oct. 28, 1971 Germany............................ 2153758

[52] U.S. Cl.............................. 264/.5; 252/301.1 R; 252/408
[51] Int. Cl.².......................................... G21C 21/00
[58] Field of Search............ 252/301.1 R, 301.1 W, 252/408; 264/.5; 250/252, 303

[56] References Cited
UNITED STATES PATENTS

| | | | |
|---|---|---|---|
| 3,265,627 | 8/1966 | Clark et al. ................. | 252/301.1 W |
| 3,314,893 | 4/1967 | Hoffman ...................... | 252/301.1 L |
| 3,340,201 | 9/1967 | Kirchner...................... | 252/301.1 R |
| 3,373,116 | 3/1968 | Sun et al. ..................... | 252/301.1 L |
| 3,740,241 | 6/1973 | Bromer et al...................... | 252/408 |
| 3,764,805 | 10/1973 | Alley.................................. | 250/252 |

FOREIGN PATENTS OR APPLICATIONS 968,763  9/1964  United Kingdom......... 252/301.1 W

*Primary Examiner*—Verlin R. Pendegrass
*Assistant Examiner*—Peter A. Nelson
*Attorney, Agent, or Firm*—Kenyon & Kenyon Reilly Carr & Chapin

[57] ABSTRACT

In preparing test specimens for analysis, especially by X-ray fluorescence, the materials to be tested are comminuted and then dissolved in molten phosphates that are molten at elevated temperatures (several hundred degrees Centigrade) but solid at room temperature, and are subsequently cast into the required specimen form.

6 Claims, 1 Drawing Figure

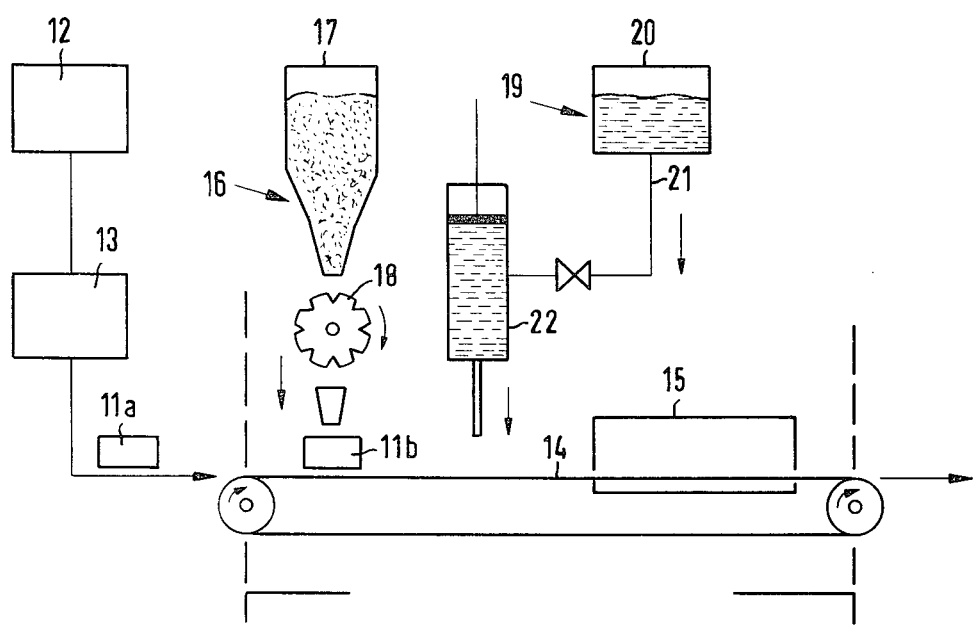

METHOD FOR PREPARING TEST SPECIMENS FOR ANALYSIS

This invention relates to a process, and apparatus for performing it, for the preparation of test specimens for analysis, e.g., for X-ray fluorescence analysis, particularly of nuclear reactor fuel and breeder materials.

In many fields of technology, continuous monitoring of the composition of the manufactured products is necessary, e.g., in the metallurgical and cement industries, and particularly in the manufacture of nuclear fuel, where it is most important to control continuously the uranium and plutonium content in the powdered raw materials employed in manufacturing the nuclear fuel pellets, or in the pellets themselves. Although chemical analytical methods are known for this purpose, they are impractical in commercial manufacturing because of the long time they require.

The already-known method of X-ray fluorescence analysis, however, is considerably better suited for such continuous minitoring tests, especially since its attainable accuracy of analysis is greater. A prerequisite for conducting such a test method, however, is the shaping of the material into a form suitable for X-ray fluorescence analysis, where however, stringent requirements are placed on the rapidity and simplicity of carrying out the method, and on the homogeneity of the resulting test specimen.

Dissolution of the specimen material in mineral acids is known. This procedure, however, is impractical, as it requires excessive time and is attended by the possibility of contamination of the test equipment as a result of handling liquid radioactive samples. Direct analysis of the nuclear fuel materials, e.g., of the fuel pellets, also does not lead to satisfactory results because of their inhomogeneity.

The problem therefore arises to find a fusion process for the material samples to be tested, which can be carried out simply and rapidly and by means of which test specimens can be prepared in solid form which are practically free of stress and assure ease of handling without problems, such as mechanical breakage or contamination of equipment.

An object of this invention is to provide an improved process for preparing samples for mechanical analytical analysis, especially by X-ray fluorescence.

A further object is to provide apparatus for performing the process in a continuous manner.

According to the invention, this problem is solved by dissolving a comminuted sample of the material to be tested by fusion treatment in phosphates which are liquid in the range of several hundred degrees Centigrade but are solid at room temperature, and then shaping the specimen into the required form by casting. Thus, the process invention comprises dissolving a sample of material to be analyzed in a molten phosphate, especially an ammonium phosphate, such phosphate being characterized by being normally solid at room temperature and melting at an elevated temperature, preferably above 200°C, and thereafter casting the resulting mixture of dissolved sample and phosphate into a shaped form. The phosphate is sometimes referred to hereinafter as the fusion agent.

It has been discovered that ammonium phosphate, particularly diammonium phosphate $(NH_4)_2HPO_4$, is particularly suitable for the process, because it solidifies in vitreous form which results in desirably smooth and durable specimen surfaces obtainable through the use of suitable molds.

Of great importance for the quality of the specimen resulting after the cooling of the melt is the temperature of the molten phosphate during the fusion process. The latter preferably is in the range of about 350° to 450°C. The best results have been obtained with melt temperatures of about 400°C. Solidification occurs at temperatures of only about 120°C. A special temperature treatment, for instance, by slow cooling or similar measures, is not necessary. On the other hand, it is possible to make these preparations plastically deformable by briefly heating to temperatures of about 100°C and then allowing them to resolidify to a vitreous, solid consistency. When the temperature of the molten phosphate is below the temperature range mentioned, the resulting specimens are not firm enough and can be plastically deformed by only light pressure. Above this temperature range, the resulting test specimens are partially crystalline which when solidified are non-homogeneous, and hence are therefore of limited suitability for use in X-ray fluorescence analysis.

The amount of the phosphate fusion agent is preferably at least 50 times, by weight, greater than the sample to be analyzed, in order that complete dissolution of the sample material in the ammonium phosphate takes place. Twenty to 30 minutes have been found to be sufficient as the dissolution time. Inasmuch as ammonia and water vapor escape during the fusion treatment, there is a loss of weight (mass) of the combined phosphate and sample, and thus a change in the concentration of the material to be tested in the test specimen. In order to obtain reproducible and comparable values with the method of analysis, it is therefore necessary to keep this weight reduction always the same during the preparation of the test specimens, i.e., to standardize the specimen preparation process by employing a uniform treatment (dissolution) time and temperature. This may be accomplished, for instance, through the use of a continuous furnace, the temperature profile of which can be adjusted accurately and in which the rate of travel of the crucibles containing the molten specimens can be adjusted and kept constant.

The apparatus employed in conducting the process is shown schematically in the attached FIGURE. The apparatus comprises a plurality of crucibles 11a, 11b. These are adapted to receive a small amount of a sample of material to be incorporated into a test specimen. The material may be comminuted in a mill 12. The amount of material placed in a specific crucible (e.g., crucible 11a) is determined by weighing device 13.

The apparatus includes a conveyor means, here depicted as conveyor belt 14, a furnace 15, and fusion agent storage and metering means 16.

The fusion agent storage and metering means 16 comprises fusion agent storage bin 17 and fusion agent metering means 18. The latter is adapted to automatically release into a crucible a predetermined amount of fusion agent. The metering means 18 is adapted to release the fusion agent into the crucible when the crucible, disposed on conveyor belt 14, is at a predetermined location in relation to said metering means.

The apparatus optionally comprises an internal standardizing agent storage and metering means 19 comprising a storage container 20 connected through valved-conduit means 21 to standardizing agent metering means 22. The latter preferably is located intermediate between fusion agent metering means 18 and furnace 15, and is adapted to release a predetermined amount of standardizing agent into the crucible when the crucible, disposed on conveyor belt 14, is at a predetermined location in relation to said metering means.

Furnace 15 is adapted to heat the crucibles (and their contents) to a predetermined temperature, in the range of several hundred degrees Centigrade.

The conveyor belt 14 is adapted to transport the crucibles into position to receive the fusion agent, and then to receive the standardizing agent, if any is to be employed, and subsequently to transport the crucibles into and out of the furnace, maintaining each crucible within the furnace for a predetermined length of time. The conveyor means may be adpated to move continuously, or intermittently, stopping briefly to allow release of the fusion agent and standardizing agent into the crucibles.

In conducting the process with such apparatus, the sample to be tested is first comminuted in mill 12 and then weighed into a crucible 11a by means of a weighing device 13. The crucible with the powdered sample material is then placed on the conveyor belt 14 and the fusion agent, e.g., ammonium phosphate, is added to the crucible 11b (having advanced along belt 14) from the metering device 18. A second metering device 22 meters into the crucible a measured amount of an internal standard in the form of a thorium solution, which is contained in supply tank 20. Metering device 22 may consist of a plunger burette, as shown schematically. Subsequently, the crucible travels through continuous furnace 15 on the conveyor belt 14 at a constant speed. At the exit of the furnace, the crucible with the melt of sample material and fusion agent in it is removed from the conveyor belt and the melt is poured (cast) into molds, not shown. There, it solidifies to form a solid, vitreous test specimen which can then be introduced immediately to the analytical equipment. The process may be operated continuously, employing a plurality of crucibles.

If the test specimens are to be stored for an extended period of time, it is advisable to seal the storage containers hermetically to provide a drying agent, e.g., phosphorus pentoxide, for drying the air in the container. This is advisable as the test specimens are slightly hygroscopic. If they no longer need to be stored, they can be dissolved in water after the analytical measurements are completed, and valuable or radioactive ingredients recovered in a reprocessing facility.

The addition of an internal standard, for instance, in the form of the above-mentioned thorium solution, makes it possible to monitor the calibration of the X-ray fluorescence apparatus continuously. If the sample material contains plutonium, the entire apparatus for carrying out the method can be located without difficulty in a box-like housing which is shielded against alpha-radiation. The mount for the specimens of the X-ray fluorescence spectrometer optionally may also be located within the housing, while the other parts of the spectrometer may be arranged outside the alpha-radiation shielding.

The simplest molds have been found suitable for making the test specimens. These may consist, for instance, of an aluminum ring which is simply placed on a ground brass plate rubbed (thinly coated) with silicon oil. It is not necessary to surface-finish the solid test specimens taken from these molds. The test specimens are particularly well suited if L-fluorescence radiation is excited by the spectrometer. If, however, thick-walled molds are used, the bottom of which is ground absolutely flat and which are not separated from the solidified melt, excitation of K-fluorescence radiation by, for instance, means of radio-nuclide sources, is necessary.

The exposed excitation surfaces obtained with the first-mentioned form of specimens for X-ray spectrometry can be covered for protection with foil or thin sheets which are held in position by residual silicon oil still present on the surface of the specimen.

The homogeneity of the test specimens is excellent; it was tested for plutonium distribution on plane radiation surfaces by means of alpha auto-radiography.

With the arrangements for carrying out the method as described herein, a total time of about 60 minutes is required for a complete analysis. However, since normally several samples are prepared and measured in short intervals, the effective working time required per test specimen is reduced to about 15 minutes.

Besides nuclear fuel materials, a number of other technical products such as, for instance, cement materials, copper alloys, etc., may be rapidly and completely dissolved in ammonium phosphate under the conditions described and can be cast to form specimens for X-ray spectrometry. Other substances, such as for instance, $NH_4$, $HF_2$ or $NH_4NO_3$, may also be mixed with the fusion agent.

As already noted, the solidified test specimens dissolve readily and rapidly (within 10 to 15 minutes) in warm water or dilute mineral acids. This means that fusion digestion of nuclear fuel materials, or of the other materials mentioned above, is not limited only to X-ray spectrometry, but may be used to advantage also for other analytical methods, in which the presence of phosphates does not interfere. The determination of uranium and plutonium in their oxides by potential-controlled coulometry or by redox titration should be mentioned as examples of such other analytical methods.

Having thus described the invention, we claim:

1. The process for preparing test specimens for X-ray analysis, which process comprises mixing together a radio active sample material to be analyzed, a molten phosphate which is normally solid at room temperature and melts at a temperature above 100°, said molten phosphate being at least 50 times by weight greater than the amount of said sample and a substance which serves as an internal standard for X-ray analysis, and forming the resulting mixture into a shaped form suitable for X-ray analysis.

2. The process of claim 1 in which said phosphate is $(NH_4)_2 HPO_4$.

3. The process of claim 1 in which said molten phosphate is ammonium phosphate at a temperature in the range of about 350° to 450°C.

4. The process of claim 3 in which the mixture is formed at a temperature of about 150°C.

5. The process of claim 1 in which said sample is in comminuted form before being added to said molten phosphate.

6. The process for preparing test specimens for X-ray analysis, which process comprises dissolving a radioactive sample of material to be analyzed in a molten ammonium phosphate, said phosphate being at a temperature of about 350°–450°C, wherein the amount of molten phosphate is at least 50 times, by weight, greater than the amount of said sample, mixing therewith a substance which serves as an internal standard for X-ray analysis, and casting the resulting mixture consisting essentially of said dissolved sample, phosphate and internal standard substance into a water-soluble shaped form suitable for X-ray analysis.

* * * * *